Figure 1:
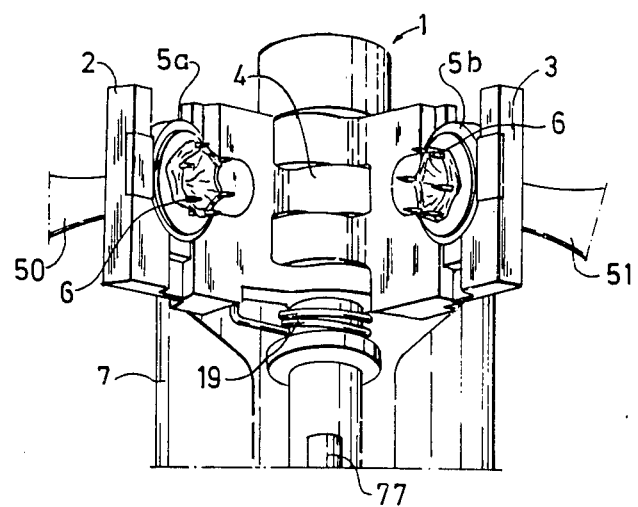

United States Patent [19]

Berggren et al.

[11] Patent Number: 4,624,257
[45] Date of Patent: Nov. 25, 1986

[54] SURGICAL INSTRUMENT FOR PERFORMING ANASTOMOSIS

[76] Inventors: Anders Berggren, Bergdalsgatan 6, Linkoping s-582 45; Hakan A. E. Rohman, Vitsippestigen 4, Mantorp s-590 20; Leif T. Ostrup, Onkel Adamsgatan 10, Linkoping s-582 35, all of Sweden

[21] Appl. No.: 588,100
[22] PCT Filed: Jun. 17, 1983
[86] PCT No.: PCT/SE83/00253
    § 371 Date: Feb. 21, 1984
    § 102(e) Date: Feb. 21, 1984
[87] PCT Pub. No.: WO84/00102
    PCT Pub. Date: Jan. 19, 1984

[30] Foreign Application Priority Data

Jun. 24, 1982 [SE] Sweden ................. 8203966

[51] Int. Cl.[4] ............... A61B 17/04; A61B 17/08
[52] U.S. Cl. ...................... 128/334 C; 128/335
[58] Field of Search ............. 128/334, 334 C, 335

[56] References Cited

U.S. PATENT DOCUMENTS

| | | |
|---|---|---|
| 1,151,300 | 8/1915 | Soresi . |
| 1,918,890 | 7/1933 | Bacon . |
| 2,434,030 | 1/1948 | Yeomans ............. 128/346 |
| 2,453,056 | 11/1948 | Zack ................. 128/334 |
| 2,638,901 | 5/1953 | Sugarbaker ........... 128/334 |
| 3,254,650 | 6/1966 | Collito .............. 128/334 |
| 3,254,651 | 6/1966 | Collito .............. 128/334 |
| 3,258,012 | 6/1966 | Nakayama et al. ...... 128/334 |
| 3,265,069 | 8/1966 | Healey, Jr. et al. ... 128/334 |
| 3,316,914 | 5/1977 | Collito .............. 128/334 |
| 3,409,914 | 11/1968 | Jones . |
| 3,456,965 | 7/1969 | Gajewski et al. ...... 285/260 |
| 3,484,121 | 12/1969 | Quinton .............. 285/242 |

List Continued on next page.

FOREIGN PATENT DOCUMENTS

| | | |
|---|---|---|
| 899749 | 5/1972 | Canada .............. 128/122 |
| 908529 | 8/1972 | Canada .............. 128/122 |
| 1057729 | 5/1959 | Fed. Rep. of Germany . |
| 2101282 | 7/1972 | Fed. Rep. of Germany . |
| 2200981 | 7/1973 | Fed. Rep. of Germany . |
| 2600142 | 7/1977 | Fed. Rep. of Germany . |
| 2657255 | 6/1978 | Fed. Rep. of Germany . |
| 2316910 | 2/1977 | France . |
| WO82/01644 | 5/1982 | PCT Int'l Appl. . |

OTHER PUBLICATIONS

"Anastomoses De Petits Vaisseaux Sans Sutures, Avec l'Instrumentation De Nakayama", La Presse Medicale, vol. 72, No. 20, Jun. 13, 1961, pp. 1657–1661.
"Anastomosis of Small Veins With Suture or Nakayama's Apparatus, A Comparative Study", Leif T. Ostrup, Scand J. Plast Reconstr. Surg., 10:9–17, 1976.
"Microvascular Surgery, Techniques and Applications in Plastic Surgery", Leif T. Ostrup et al, Scand J. Plast Reconstr. Surg. 10:18–28, 1976.
"Extended Laryngopharyngectomy for Carcinoma of the Laryngopharynx and the Cervical Oesophagus (Use of a Free Graft of Large Intestine)", P. Chrysospathis et al, J. Laryngol 79, 233–236 (1965).
"L'anastomosose des arteres de tres petit diametre a Primary Examiner—Richard C. Pinkham
Assistant Examiner—Benjamin Layno
Attorney, Agent, or Firm—Woodcock Washburn Kurtz Mackiewicz & Norris

[57] ABSTRACT

In surgery, especially in microsurgery, the joining of blood vessel ends or other tubular organs, anastomosis, consumes a considerable part of the time. In order to carry out anastomosis rapidly and reliably a surgical instrument (1) is provided with two clamping means (2, 3), each being arranged to support a fastening means (5a, 5b) consisting of a ring with axially directed pins (6). The clamping means (2, 3) are rotatably connected to the instrument and can be actuated by mechanism (i.a. 7) to be turned towards each other to join the fastening means (5a, 5b) and vessels or organs (50, 51) threaded onto these. The invention also relates to fastening means 5a, 5b) shaped in such a manner that they are retained in the clamping means (2, 3) of the instrument until the joining is accomplished.

35 Claims, 9 Drawing Figures

U.S. PATENT DOCUMENTS

| | | |
|---|---|---|
| 3,514,791 | 6/1970 | Sparks ............................................ 3/1 |
| 3,552,626 | 1/1971 | Astafiev ................................... 227/76 |
| 3,561,448 | 2/1971 | Peternel ................................. 128/334 |
| 3,606,808 | 9/1971 | Bowden .................................... 82/40 |
| 3,628,813 | 12/1971 | Lee et al. ................................ 285/31 |
| 3,683,926 | 8/1972 | Suzuki .................................. 128/334 |
| 3,713,441 | 1/1973 | Thomas ............................. 128/214 R |
| 3,742,933 | 7/1973 | Bucalo ................................. 128/1 R |
| 3,771,526 | 11/1973 | Rudle .................................. 128/334 |
| 3,774,615 | 11/1973 | Lim et al. ............................. 128/334 |
| 3,831,584 | 8/1974 | Bucalo ................................. 128/1 R |
| 3,833,940 | 9/1974 | Hartenbach ......................... 128/334 |
| 3,877,435 | 4/1975 | Bucalo .................................. 128/334 |
| 3,880,137 | 4/1975 | Bucalo ................................. 128/1 R |
| 3,882,862 | 5/1975 | Berend ............................. 128/214 R |
| 3,908,662 | 9/1975 | Razgulov et al. ..................... 128/334 |
| 3,945,052 | 3/1976 | Liebig ....................................... 3/1 |
| 3,974,835 | 8/1976 | Hardy .................................. 128/334 |
| 3,990,434 | 11/1976 | Free ..................................... 128/1 R |
| 4,055,186 | 10/1977 | Leveen ................................. 128/334 |
| 4,198,982 | 4/1980 | Fortner et al. ....................... 128/334 |
| 4,200,107 | 4/1980 | Reid . | |
| 4,214,586 | 7/1980 | Mericle ................................ 128/334 |
| 4,289,133 | 9/1981 | Rothfuss .............................. 128/334 |
| 4,294,255 | 10/1981 | Geroc .................................. 128/334 |
| 4,306,545 | 12/1981 | Ivan et al. ............................ 128/1 R |
| 4,350,160 | 9/1982 | Kolesov et al. ...................... 128/334 |
| 4,505,272 | 3/1985 | Utyamyshev et al. .............. 128/305 |

OTHER PUBLICATIONS l'aide du bouton anastomotique de Nakayama", P. Replumaz et al, Lyon Chir 60, 263 (1964).

"Internal Mammary-Coronary Artery Anastomoses, A Method Utilizing Nakayama's Instrument for Small Vessel Anastomoses", Koki Abe, M.D. et al, J. Thorac Cardiovsc Surg. 51, 808-820 (1966).

"Observations on the Technique of Microvascular Anastomosis Using the Nakayama Instrument", R. B. Bradshaw, M. D. et al, Proc. Can Otolaryng. Soc., 23, 1969, pp. 96-105.

"A New Vascular Anastomosing Instrument and Its Clinical Application", Komei Nakayama M.D. et al, Clin Ortho Rel Res 29, 123-131 (1963).

"Unilink Instrument System for Fast and Safe Microvascular Anastomosis", Leif T. Ostrup M.D., The Unilink Company.

Holt et al, "A New Technique for End-to-End Anastomosis of Small Arteries", *Surgical Forum*, 11:242 (1960).

Nakayama et al, "A Simple New Apparatus for Small Vessel Anastomosis (Free Autograft of the Sigmoid Included)", *Surgery*, vol. 52, No. 6, pp. 918-931 (Dec. 1962).

SURGICAL INSTRUMENT FOR PERFORMING ANASTOMOSIS

CROSS-REFERENCE TO RELATED APPLICATION

This application, which is based upon PCT/SE83/00253, June 17, 1983, and which claims priority from Swedish application No. 8203966-0 filed June 24, 1982, is related to U.S. application Ser. No. 516,462, filed July 22, 1983.

The present invention concerns a surgical instrument for joining two vessel ends or other tubular organs and establishing liquid connection between them, i.e. anastomosis, by the aid of annular clamping means, anastomosis rings, provided with axially directed pins, on which the vessel ends are threaded before the joining. The invention also concerns anastomosis rings to be used in anastomosis with this surgical instrument. The instrument and the anastomosis rings are shaped and adapted to be utilized mainly in microsurgery.

From the U.S. Pat. No. 3,258,012, Nakayama et al, it is previously known to join two blood vessel ends by means of a pair of needle discs having alternately spaced projecting needles and holes for these on an annular base element. For the joining of two blood vessel ends by means of these needle discs or anastomosis rings two forceps are used retaining the needle discs during threading of the blood vessel end into the needles and holding the needle disc in a suitable position so that it can be secured to the needle disc on the other vessel end by the needles being pressed through the holes on the opposite needle disc and bent when the guided forceps are pressed together.

One difficulty in using Nakayama's method is that two different separate forceps are needed to perform the anastomosis. The guides in these two forceps are to be fitted into each other before the two forceps are pressed together by means of a third instrument. Another difficulty may arise as the tips of the blades of the two anastomosis forceps i.a. carry one of the guides, why they extend considerably outside the needle disc which may create problems as the surgical area is limited.

Another difficulty in the known method is that the needles of the needle discs are intended to be bent around the opposite needle disc, why they are rather long. At small vessel dimensions they will be easily exposed to bending and wrong alignment in handling and threading of the blood vessel end, and a malfunction may be the result due to the fact that during the compression all needles are not brought through the correct hole in the opposite needle disc.

Said difficulties are overcome effectively by means of an instrument and anastomosis rings according to the invention. Thus, one object of the invention is to provide a surgical instrument retaining two anastomosis rings while threading the vessel ends and embodied so that the anastomosis rings are directed towards each other and that the instrument, moreover, comprises means for pressing the anastomosis rings together without any requirement of additional tools or instruments.

It is also an object of the invention to provide anastomosis rings being adapted to the surgical instrument according to the invention.

Another object of the invention is to achieve an anastomosis instrument and anastomosis rings being adapted for the joining of vessels having small dimensions and for narrow surgical areas.

These and other objects are met by means of an anastomosis instrument and anastomosis rings having the characterizing features defined in the claims.

Figure 2:
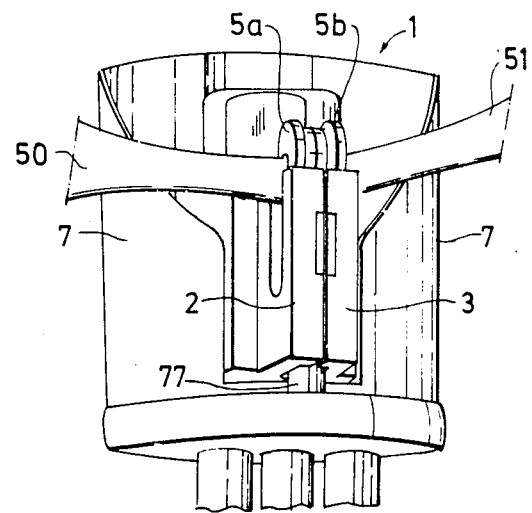
Figure 3:
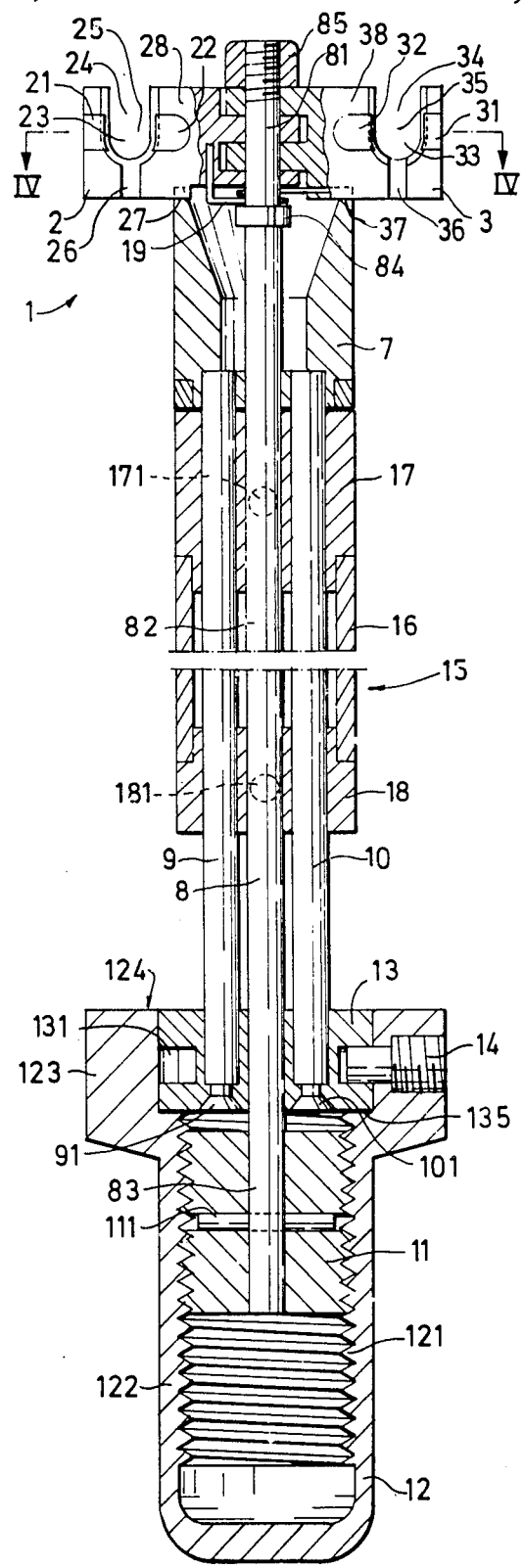
Figure 4:
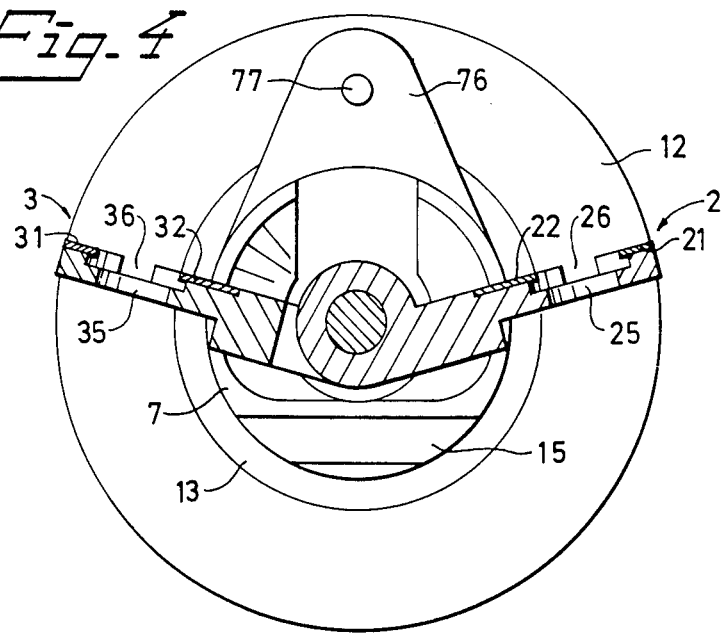
Figure 5:
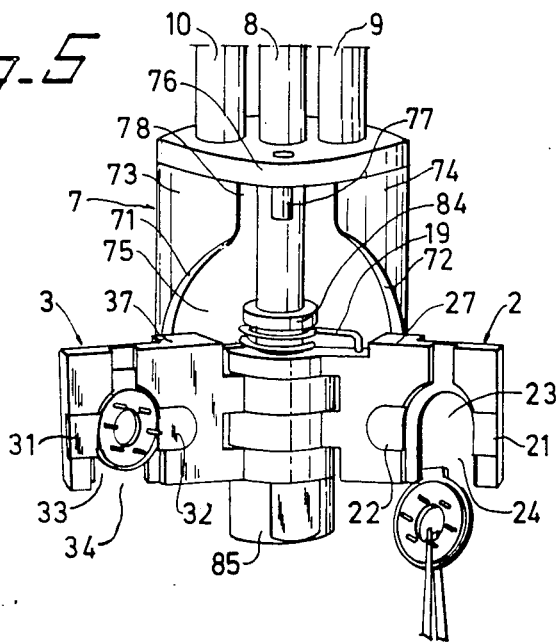
Figure 6:
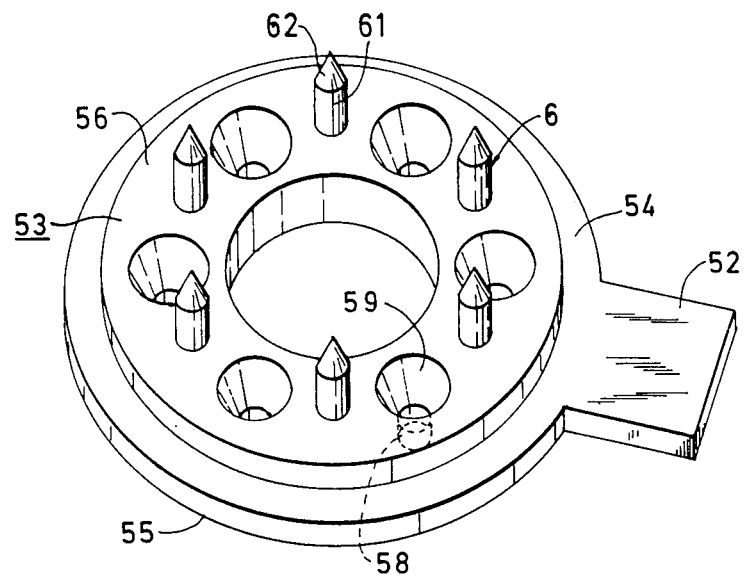
Figure 7:
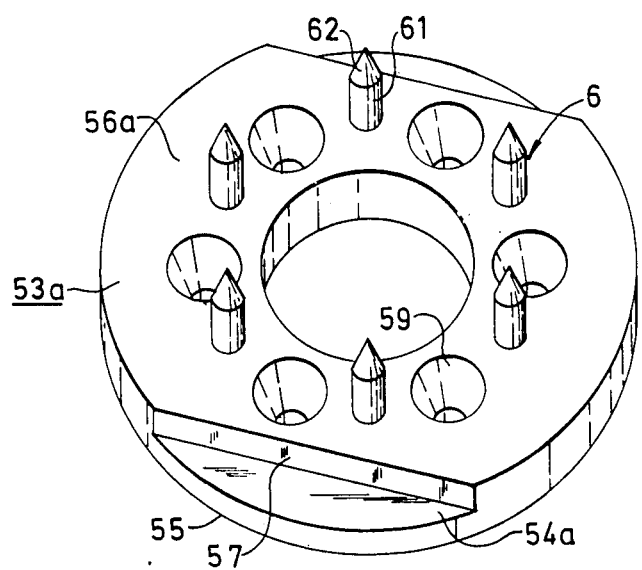
Figure 8:
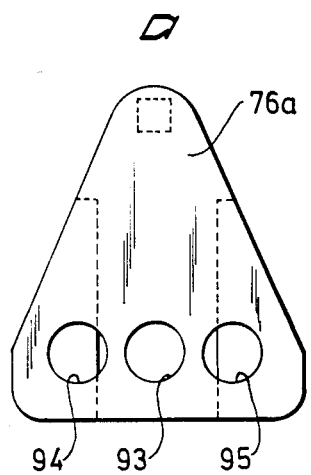
Figure 8:
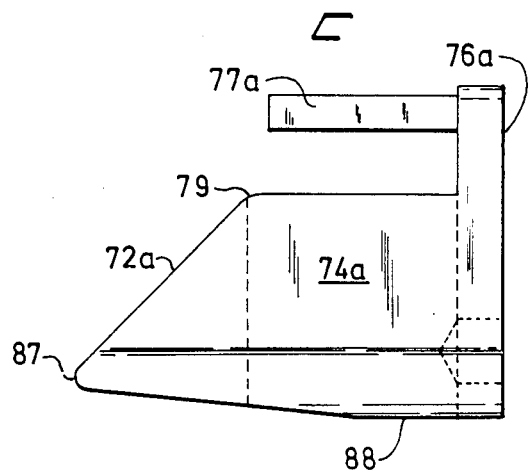
Figure 8:
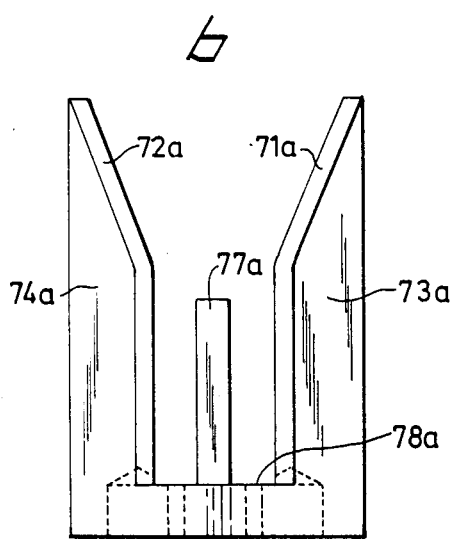

The invention will be described more in detail in connection with the embodiments shown in the drawings where FIG. 1 shows an enlarged portion of an instrument according to the invention at one moment of its use, FIG. 2 shows the same part of the instrument as FIG. 1 at a later moment, FIG. 3 shows an enlargement, partly in section, of the whole instrument of FIGS. 1 and 2 with a central portion cut off, FIG. 4 shows the section IV—IV in FIG. 3. as further enlarged, FIG. 5 shows enlarged parts of the front portion of the instrument, FIG. 6 shows a great enlargement of an embodiment of a fastening means according to the invention, FIG. 7 shows a great enlargement of another embodiment of the fastenings means according to the invention, FIGS. 8a–c shows an alternative embodiment of the guide bushing of the instrument according to FIGS. 1-5.

FIGS. 1 and 2 illustrate the utilization of a surgical instrument of the invention while joining two vessels with fastening means according to the invention. FIGS. 1 and 2 show only those parts of the instrument 1 forming the end of the instrument located at the surgical area. Thus, the instrument 1 is provided with two clamping means 2,3 which by the aid of a hinge 4 are rotatable around a longitudinal axis of the instrument. According to the invention each clamping means supports a fastening means 5a, 5b. In a position of the clamping means 2,3, where these have been turned apart almost 180° in the hinge, the ends of the blood vessels 50 and 51 have been threaded from below through the centre holes of the fastening means 5a and 5b and unfolded and threaded onto the pins 6 of the fastening means. By the actuation of a mechanism the guide bushing 7 is moved lengthwise of the instrument so that the clamping means 2,3 are turned towards each other, the clamping means 2,3 passing a position according to FIG. 1 until the fastening means 5a,5b supported by the clamping means 2,3 have been moved together completely, the pins 6 of the fastening means being engaged with the corresponding holes in the opposite fastening means. When the guide bushing 7 is further displaced a pusher 77 connected with the guide bushing will push the joined fastening means 5a,5b and the vessels 50,51 out of the joined clamping means 2,3, as shown in FIG. 2.

As is apparent from FIG. 3 the clamping means 2,3 are rotatable around a carrier rod 8 at its front end 81, said rod being parallel with the longitudinal axis of the instrument. A longitudinal handle 15, consisting of a tubular casing 16 sealed with end portions 17,18, is attached to the central portion 82 of the carrier rod. The carrier rod 8 is passed through central bores in the end portions 17 and 18 and is fixed to these by stop screws 171,181. A carrier 11 is fixed by means of a tubular pin 111 through a diametrical hole in the rear end 83 of the carrier rod 8. The carrier 11 consists of a cylindrical body with threads on the mantle surface, a central hole receiving the carrier rod 8 and a diametrical hole adapted to the tubular pin 111. The thread of the carrier 11 engages the internal thread 121 of a capped nut 12, which consists of a rear cylindrical portion 122 with gripping surfaces around the mantle surface, and a front cylindrical portion 123 of a larger outside diameter and a greater material thickness. The capped nut is internally threaded in the main portion of its length, except for a portion at the front end surface 124 of the capped nut where the capped nut has an unthreaded larger inside diameter adapted to a guide 13 of a substantially circular-cylindrical form so that the guide 13 is quite countersunk in the front end surface 124 of the capped nut 12. There is an annular groove 131 in the mantle surface of the guide 13, in which pin screws 14, screwed radially into the front portion 123 of the capped nut, are arranged to run. The guide 13 is provided with a central hole through which the carrier rod 8 is movably arranged, and on both sides of the central hole other holes are arranged, through which two guide rods 9 and 10 parallel with the carrier rod are fixed to the guide 13 by means of screws 91 and 101. An insert 135 in the form of a washer is arranged in the capped nut 12 against the interior end surface of the guide 13. The guide rods 9 and 10 run through holes in the end portions 17 and 18 of the handle 15 and the front ends of the guide rods are fixed in the guide bushing 7. A displacement mechanism of the guide bushing 7 is formed by the carrier rod 8, the guide rods 9 and 10, the carrier 11, the capped nut 12, the guide 13 and the pin screws 14, which mechanism moves the guide bushing 7 longitudinally in the instrument when the capped nut 12 is turned.

The guide bushing 7 (FIG. 5) is formed with two curved portions 73 and 74, the outer surfaces of which form parts of a cylinder having the same central axis as the carrier rod 8. The two curved portions 73 and 74 are connected with a substantially flat bottom portion 75 under the carrier rod 8 and a substantially flat end portion 78 against the handle 15 of the instrument. The curved portions of the guide bushing 7 are bevel cut at a sharp angle, preferably about 45° to the central axis, to form guide surfaces 71 and 72, on which the clamping means 3 and 2, respectively, abut with guide surfaces 37 and 27, respectively, under the influence of the torsion spring 19. An end piece 76 is arranged at the end portion 78 of the guide bushing 7, said end piece 76 projecting above the curved portions 73 and 74 of the guide bushing. On the end piece is mounted a pusher 77 in the form of a cylindrical pin directed to the front end of the instrument. The two fixing members 2 and 3 are each made of a plate 28, 38 provided with a pair of annular elements, the annular elements from the two clamping means being alternately threaded on to the front end 81 of the carrier rod 8 so that a hinge is formed by the two clamping means and the carrier rod. In order to keep the clamping means in position together with the torsion spring 19, the carrier rod is provided with a fixed ring 84 spaced from the front end 81 and a nut 85 screwed on to the end. The two plates 28 and 38 are mirror images of each other. They have substantially flat upper surfaces, the extensions of which intersect along or close to the central line of the carrier rod 8. Each plate 28,38 has at its upper surface a recess 23,33 in which a clamping means can be placed so that it is countersunk in the plate with essentially all of its ring. The recess 23,33 is substantially a circular-cylindrical milling with an opening 24,34 against the front end of the plate in the whole diameter width, so that a clamping means can be pushed in along the plane of the plate.

Stop means 21, 22, 31, 32 are arranged in the inserted position of the ring on both sides of the ring, which stop means are countersunk at the upper surfaces of the plates and project somewhat beyond the recess 23,33 so that they cooperate with shoulders on the fastening means and maintain these in position for connection. Below the recesses 23,33 and their openings 24,34, the plates are formed with an additional recess 25,35 through the plate material with a smaller diameter and width but sufficient for the vessel dimension. Moreover, there are grooves 26,36 backwards from the recesses 23 and 33 being adapted to guide means on the fastening means.

One embodiment of a fastening means of the invention is apparent from FIG. 6. The fastening means consists of a ring 53 with a number of axially directed pins 6 and intermediate holes 58 distributed on a circumference around the centre of the ring. The ring 53 has a lower end surface 55 and an upper end surface 56 which are plane-parallel, and the axial pins are secured to the ring and extend through the upper end surface 56. The ring 53 has a central hole through which the vessel end to be joined can be brought and the periphery of the ring forms the main portion of a cylinder surface. A guide element 52 directed radially outwards extends from the periphery of the ring. The central line of the guide element is preferably directed so that it divides the angle between a pin and a hole into equal parts, and in this way the pins in rings with pins directed towards the same point are correctly guided when joined. A shoulder 54 parallel to the end surfaces of the ring is arranged along the periphery of the ring at a definite distance from the lower end surface 55. In the embodiment shown, the shoulder 54 is arranged around the whole ring but can also be arranged only at certain portions of the ring, at least two diametrically opposed portions being provided with a shoulder. The holes 58 of the ring are preferably shaped with a conically widened portion 59 at the upper end surface 56 in order to guide the pins 6 into the holes 58. The pins 6 of the fastening means has a portion 61 of a substantially even thickness and a conical tip 62. The portion 61 of the pin extends outside the upper end surface 56 of the ring at least for a distance being equal to and preferably somewhat more than the thickness of the ring. The holes 58 of the ring are adapted to the dimension of the portion 61 of the pins so that pins forced into the holes 58 are steadily kept therein. The pins are preferably secured in the ring by casting.

According to the embodiment of the fastening means shown in FIG. 7 the shoulder 54 arranged along the whole periphery of the ring has been replaced by the shoulders 54a arranged only at two diametrically opposed portions of the ring 53a. The countersunk parts of the ring at the shoulders 54a are delimited by substantially flat and parallel surfaces 57 from the other parts of the ring, the upper end surface 56a and the lower end surface 55 of which are substantially plane-parallel. The distance between the surfaces 57 delimiting the two diametrically opposed shoulders 54a being adapted to the distance between the stop means 21 and 22, 31 and 32 respectively of the clamping means 2,3 of the instrument 1, the ring 53a will be put carefully in position in the clamping means 2,3, the ring 53a not necessarily being provided with any element corresponding to the guide element 52 of the embodiment according to FIG. 6. The embodiment according to FIG. 7 may also be provided with an element corresponding to the guide element 52, preferably designed like that, but with the same thickness as the ring 53a. The shape and the position of the pins 6,61,62 and the holes 58,59 are identical at the two embodiments according to FIGS. 6 and 7.

The instrument of the invention must really not be changed in order to be used also to the fastening means according to FIG. 7. In order to obtain the best mode of operation the sides of the stop means 21,22,31 and 32 directed inwards against the fastening means should be straight and the length of the pusher 77 should be adjusted to the presence of a guide element 52 or a corresponding element on the fastening means.

The alternative embodiment according to FIGS. 8a–c may substitute the guide bushing 7 in the instrument according to FIGS. 1–5 without the need of any other changes of the instrument. The main differences are that the guide surfaces 71a and 72a are substantially straight and that the guide bushing is made open in the bottom by elimination of the bottom portion 75. According to this embodiment an improvement of the instrument is obtained concerning cleaning and sterilization at the same time as it gives better access to the surgical area and is easy to make. Thus the embodiment is constructed with an end piece 76a constituted by a plate of a mainly isosceles, triangular form with three holes 93,94 and 95 arranged upon a line on a distance from the base line. The carrier rod 8 is meant to run through the central hole 93 and the guide rods 9 and 10 shall be fixed in the two outer holes 94 and 95, for instance by soldering.

A pusher 77a with a rectangular cross-section projects at the right angle to one side surface 78a of the end piece 76a and close to its upper apex. Also projecting at the right angle from the side surface 78a are two side portions 73a and 74a with substantially triangular cross-sections. Thus, the side portion 74a is shaped with a substantially flat outer side surface connecting with the central and lower part of one side of the periphery of the end piece 76a and it is also delimited by an inner surface parallel to the axis of symmetry of the end piece 76a and a bottom surface connecting with the base of the end portion 76a. The side portion 74a consists of a portion with a substantially constant cross-section extending from the end piece 76a and somewhat further than the pusher 77a, the side portion 74a thereafter tapers from the break point 79 to the point 87, the inner surface of the side portion 74a being broken outwards with an arc of about 22° and the upper edge of the side portion 74a being broken downwards with an arc of about 45°. The upper edge of the side portion 74a is bevelled to a narrow guide surface 72a running from the point 87 to the break point 79 and further to the end piece 76a with a substantially even width. The side portions 74a may be bevelled at a small arc, preferrably about 4°, from a position 88 on the base surface somewhat apart from the end piece 76a to the point 87. The opposite side portion 73a is a reflection of the side portion 74a in relation to the plane of symmetry through the end piece 76a and the pusher 77a.

The embodiment according to FIGS. 8a–c may preferrably be made in one piece in a metallic material. The pusher 77a may also be made separately and be fastened in a recess in the end piece 76a, for instance by soldering, the side portions 73a and 74a may also be constructed in the same way.

The instrument of the invention is made so that sterilization thereof easily can be performed. The fastening means are made of a biocompatible material which can be sterilized and does not cause any repelling reactions. The pins of the fastening means are preferably made of stainless steel and the ring of a tissue harmless plastic material such as high density polyethylene.

The embodiments described above are only examples of an instrument and a fastening means according to the invention, which is restricted only by the claims.

We claim:

1. A surgical instrument for joining portions of generally cylindrical organs such as blood vessels and establishing connection between them (i.e. anastomosis) by using at least two couplable fasteners, each of which is selectively connectable to one of said portions to be joined, comprising:
   (a) a carrier rod;
   (b) at least two clamping means for receiving and retaining said fasteners, said clamping means mounted on said carrier rod for relative rotation around said carrier rod; and
   (c) actuating means for selectively rotating said clamping means around the axis of said rod, such that the two clamping means move towards and away from each other between at least a first position for receiving said fasteners and a second position for coupling said fasteners.

2. The surgical instrument of claim 1 wherein said clamping means retain said fasteners at locations spaced apart from the axis of said rod, whereby the relatively increased radius of rotation of said fasteners as they are rotated towards said second position minimizes the misalignment of said fasteners with respect to each other.

3. The instrument of claim 1, wherein each of said clamping means further defines a recess for slidably receiving one of said fasteners.

4. The surgical instrument of claim 3, further comprising stop means mounted on said clamping means for positioning a fastener inserted into said recess.

5. The surgical instrument of claim 4, wherein said stop means comprises a plurality of stops mounted on said clamping means, said stops extending inwardly towards said recess.

6. The surgical instrument of claim 5, wherein said plurality of stops are disposed on opposing sides of said recess.

7. The surgical instrument of claim 6, wherein said stops are complimentally configured to conform to an exterior surface of said fastener.

8. The surgical instrument of claim 3, further comprising disengaging means for pushing out coupled fasteners and their associated connected vessels from said recess.

9. The surgical instrument of claim 3, wherein said recess comprises a longitudinally extending slot.

10. The surgical instrument of claim 3, wherein said recess is keyed to the shape of said fastener to ensure that said fastener is in a couplable position upon its retention by said clamping means.

11. The surgical instrument of claim 10, wherein said fasteners are annular fasteners comprising at least one radial projection, and wherein said recess further comprises a groove configured to receive said radial projection to establish the radial orientation of said fastener.

12. The surgical instrument of claim 1 wherein said clamping means is rotatably mounted around a front portion of said carrier rod.

13. The surgical instrument of claim 1 wherein said instrument further comprises displacement means for effecting the controlled movement of said plurality of clamping means relatively with respect to said actuating means.

14. The surgical instrument of claim 13 wherein said displacement means causes controlled axial movement of said clamping means with respect to said actuating means in response to the relative rotation of portions of said displacement means.

15. The surgical instrument of claim 14 wherein said displacement means comprises an externally threaded carrier fixed to a rear portion of said carrier rod.

16. The surgical instrument of claim 15 wherein said axial displacement means comprises a cap threaded over said carrier.

17. The surgical instrument of claim 16 wherein said actuating means comprises guide bushing means movable with respect to said carrier rod in a first direction for selectively causing said plurality of clamping means to rotate towards said second position for coupling said fasteners, and wherein said axial displacement means further comprises guide rod means connected to said guide bushing means and engaging said cap for causing relative axial movement of said bushing means in response to relative axial movement of said cap.

18. The surgical instrument of claim 17 wherein said displacement means further comprises a longitudinal handle connected to said guide rod means.

19. The surgical instrument of claim 18 wherein said longitudinal handle is slidably mounted on said carrier rod.

20. The surgical instrument of claim 19 wherein said longitudinal handle comprises a tubular casing and sealing end portions.

21. The surgical instrument of claim 17 wherein said guide rod means comprises a guide slidably rotatable with respect to said cap, and a guide rod extending between said guide and said bushing means.

22. The surgical instrument of claim 21 wherein said guide has an annular track defined therein, and wherein said guide rod means further comprises a tracking pin connected to said cap for tracking in said annular track upon rotation of said cap.

23. The surgical instrument of claim 21 wherein said guide rod means comprises a plurality of guide rods.

24. A surgical instrument for joining portions of generally cylindrical organs such as blood vessels and establishing connection between them (i.e. anastomosis) by using at least two couplable fasteners, each of which is selectively connectable to one of said portions to be joined, comprising:
 (a) a carrier rod;
 (b) at least two clamping means rotatably mounted on said carrier rod for receiving and retaining said fasteners, each of said clamping means defining a recess for slidably receiving one of said fasteners;
 (c) actuating means for selectively rotating said clamping means between at least a first position for receiving said fasteners and a second position for coupling said fasteners; and
 (d) stop means mounted on said clamping means for positioning a fastener inserted into said recess, said stop means comprising a plurality of stops mounted on said clamping means, said stops extending inwardly towards said recess, being disposed on opposite sides of said recess, said stops being complementally configured to conform to an exterior surface of said fastener and being positioned along sides of said recess to permit insertion of said fastener such that at least a portion of said fastener extends beyond said stops.

25. A surgical instrument for joining portions of generally cylindrical organs such as blood vessels and establishing connection between them (i.e. anastomosis) by using at least two couplable fasteners, each of which is selectively connectable to one of said portions to be joined, comprising:
 (a) a carrier rod;
 (b) at least two clamping means rotatably mounted on said carrier rod for receiving and retaining said fasteners; and
 (c) actuating means for selectively rotating said clamping means between at least a first position for receiving said fasteners and a second position for coupling said fasteners, said actuating means comprising guide bushing means movable with respect to said carrier rod in a first direction for selectively causing said plurality of clamping means to rotate towards said second position for coupling said fasteners.

26. The surgical instrument of claim 25, wherein each of said plurality of clamping means defines a clamping means guide surface, and wherein said guide bushing means defines bushing guide surfaces which cooperate with said clamping means guide surfaces to cause said rotation upon said movement in said first direction.

27. The surgical instrument of claim 26, wherein said bushing guide surfaces are disposed at acute angles with respect to the axis of said carrier rod.

28. The surgical instrument of claim 25, further comprising disengaging means for pushing out coupled fasteners from said recess, said disengaging means comprising a pin for contacting and displacing said coupled fasteners upon continued movement of said guide bushing means in said first direction.

29. The surgical instrument of claim 28 wherein each of said plurality of clamping means has a groove defined thereon, said grooves being disposed to define a channel when said clamping means are in said second position, and wherein said pin of said disengaging means travels through at least a portion of said channel to contact said coupled fasteners.

30. The surgical instrument of claim 25 further comprising biasing means for biasing said plurality of clamping means towards said first position.

31. The surgical instrument of claim 30 wherein said biasing means comprises a torsion spring disposed around said carrier rod and engaging each of said clamping means.

32. A surgical instrument for joining portions of generally cylindrical organs, such as blood vessels, and establishing connection between them (i.e. anastomosis) by using at least two couplable fasteners, each of which is selectively connectable to one of said portions to be joined, comprising:
 (a) a carrier rod;
 (b) at least two clamping means for securing and retaining said fasteners, said clamping means mounted on said carrier rod for relative rotation around said carrier rod, said clamping means being rotatably movable around the axis of said rod, such that the two clamping means move towards and away from each other between a first position for receiving said fasteners and a second position for coupling said fasteners.

33. A surgical instrument for joining portions of generally cylindrical organs, such as blood vessels, and establishing connection between them (i.e. anastomosis) by using at least two couplable fasteners, each of which is selectively connectable to one of said portions to be joined, comprising:

(a) a carrier rod;
(b) at least two clamping means for receiving and retaining said fasteners said clamping means mounted on said carrier rod for relative rotation around said carrier rod, said clamping means being rotatably movable between a first position for receiving said fasteners and a second position for coupling said fasteners, and wherein said clamping means being rotatably movable around the axis of said rod to retain said fasteners at locations spaced apart from the axis of said rod whereby said fasteners converge along an arc when moved between said first and second positions.

34. The surgical instrument of claim 33 wherein said fasteners comprise at least two couplable rings with a plurality of axially directed pins and intermediate holes distributed around the centers thereof, said holes and said pins being configured to mate as said fasteners converge along said arc to create a fiction fit between said pins and said holes when said clamping means is moved to said second position.

35. A method of joining portions of generally cylindrical organs, such as blood vessels to establish a connection between them (i.e. anastomosis) using at least two couplable fasteners, each of which is selectively connectable to one of said portions to be joined, comprising the steps of:

(a) providing a surgical instrument comprising a carrier rod, and at least two clamping means for receiving and retaining said fasteners, said clamping means mounted on said carrier rod for relative rotation around said carrier rod, said clamping means being rotatably movable around the axis of said rod, such that the two clamping means move towards and away from each other between a first position for receiving said fasteners and a second position for coupling said fasteners;
(b) inserting each of said fasteners in a couplable orientation into each of said clamping means;
(c) connecting said portions of said organ to be joined to each of said fasteners while said clamping means are spaced apart from each other; and
(d) rotating said clamping means into said second position to couple said fasteners to thereby join said portions of said organ.

* * * * *